(12) United States Patent
Fiorella et al.

(10) Patent No.: US 8,696,622 B2
(45) Date of Patent: *Apr. 15, 2014

(54) METHOD AND APPARATUS FOR INCREASING BLOOD FLOW THROUGH AN OBSTRUCTED BLOOD VESSEL

(71) Applicant: The Cleveland Clinic Foundation, Beachwood, OH (US)

(72) Inventors: David Fiorella, East Setauket, NY (US); Henry Woo, Setauket, NY (US)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/672,445

(22) Filed: Nov. 8, 2012

(65) Prior Publication Data

US 2013/0165871 A1 Jun. 27, 2013

Related U.S. Application Data

(62) Division of application No. 13/184,359, filed on Jul. 15, 2011, now Pat. No. 8,317,748, which is a division of application No. 11/700,987, filed on Feb. 1, 2007, now Pat. No. 8,052,640.

(60) Provisional application No. 60/764,206, filed on Feb. 1, 2006, provisional application No. 60/793,588, filed on Apr. 20, 2006.

(51) Int. Cl.
*A61M 31/00* (2006.01)
*A61M 37/00* (2006.01)
*A61M 29/00* (2006.01)

(52) U.S. Cl.
USPC .............. 604/103.08; 604/103.06; 604/99.01; 604/96.01

(58) Field of Classification Search
USPC ................................ 604/96.01, 97.01, 99.01, 604/103.01–103.03, 103.05, 103.06, 604/103.08, 103.09
See application file for complete search history.

(56) References Cited

U.S. PATENT DOCUMENTS 5,222,971 A 6/1993 Willard et al.
5,693,014 A 12/1997 Abele et al.
(Continued)

FOREIGN PATENT DOCUMENTS

CA 2211516 7/1997
EP 0914807 5/1999
(Continued)

OTHER PUBLICATIONS

"Rapid Stent-Supported Revascularization in Acute Ischemic Stroke", by Fitzsimmons et al, Am. J. Neuroradiol. May 2006:27:1132-34.

*Primary Examiner* — Victoria P Shumate
(74) *Attorney, Agent, or Firm* — Fulwider Patton LLP

(57) ABSTRACT

A method of increasing blood flow through an obstructed blood vessel includes providing an expandable member substantially made of a mesh having a plurality of interstices. The expandable member is inserted into the blood vessel, positioned within the blood vessel with the proximal member end upstream of the distal member end and the member body located radially adjacent at least a portion of an obstruction, and expanded to bring at least a portion of the member body into contact with the obstruction. An outward radial force is exerted on the obstruction to dislodge at least one fragment from the obstruction and to enhance blood flow through the blood vessel past the obstruction. The at least one fragment is passed through at least one interstice of the member body in the radial direction, and is selectively retained within the expandable member.

20 Claims, 5 Drawing Sheets

(56) References Cited

U.S. PATENT DOCUMENTS

| | | | |
|---|---|---|---|
| 5,902,263 | A | 5/1999 | Patterson et al. |
| 5,928,261 | A | 7/1999 | Ruiz |
| 6,146,396 | A | 11/2000 | Konya et al. |
| 6,168,579 | B1 * | 1/2001 | Tsugita ............... 604/96.01 |
| 6,267,777 | B1 | 7/2001 | Bosma et al. |
| 6,325,815 | B1 | 12/2001 | Kusleika et al. |
| 6,443,972 | B1 | 9/2002 | Bosma et al. |
| 6,458,138 | B1 | 10/2002 | Sydney et al. |
| 6,511,492 | B1 | 1/2003 | Rosenbluth et al. |
| 6,623,452 | B2 | 9/2003 | Chien et al. |
| 6,632,241 | B1 | 10/2003 | Hancock et al. |
| 6,635,068 | B1 | 10/2003 | Dubrul et al. |
| 6,660,021 | B1 | 12/2003 | Palmer et al. |
| 6,685,722 | B1 | 2/2004 | Rosenbluth et al. |
| 6,818,006 | B2 | 11/2004 | Douk et al. |
| 6,824,545 | B2 | 11/2004 | Sepetka et al. |
| 6,843,798 | B2 | 1/2005 | Kusleika et al. |
| 6,918,921 | B2 | 7/2005 | Brady et al. |
| 7,033,375 | B2 | 4/2006 | Mazzocchi et al. |
| 7,063,707 | B2 | 6/2006 | Bose et al. |
| 7,232,432 | B2 | 6/2007 | Fulton, III et al. |
| 7,252,650 | B1 | 8/2007 | Andrews et al. |
| 7,354,419 | B2 | 4/2008 | Davies, Jr. et al. |
| 7,654,978 | B2 | 2/2010 | Wahr et al. |
| 7,691,121 | B2 | 4/2010 | Rosenbluth et al. |
| 8,100,935 | B2 | 1/2012 | Rosenbluth et al. |
| 2002/0032460 | A1 | 3/2002 | Kusleika et al. |
| 2002/0045916 | A1 | 4/2002 | Gray et al. |
| 2002/0111648 | A1 | 8/2002 | Kusleika et al. |
| 2002/0123720 | A1 | 9/2002 | Kusleika et al. |
| 2002/0133192 | A1 | 9/2002 | Kusleika et al. |
| 2002/0143360 | A1 | 10/2002 | Douk et al. |
| 2003/0074019 | A1 | 4/2003 | Gray et al. |
| 2003/0153870 | A1 | 8/2003 | Meyer et al. |
| 2003/0195554 | A1 | 10/2003 | Shen et al. |
| 2004/0039435 | A1 | 2/2004 | Hancock et al. |
| 2004/0064093 | A1 | 4/2004 | Hektner et al. |
| 2004/0082962 | A1 | 4/2004 | Demarais et al. |
| 2004/0102807 | A1 | 5/2004 | Kusleika et al. |
| 2004/0127975 | A1 | 7/2004 | Levine et al. |
| 2004/0220609 | A1 | 11/2004 | Douk et al. |
| 2005/0021075 | A1 | 1/2005 | Bonnette et al. |
| 2005/0149113 | A1 | 7/2005 | Douk et al. |
| 2005/0186242 | A1 | 8/2005 | Hunter et al. |
| 2005/0203569 | A1 | 9/2005 | Kusleika et al. |
| 2005/0240148 | A1 | 10/2005 | Cheves et al. |
| 2006/0015133 | A1 | 1/2006 | Grayzel et al. |
| 2006/0030925 | A1 | 2/2006 | Pryor |
| 2006/0149355 | A1 | 7/2006 | Mitelberg et al. |

FOREIGN PATENT DOCUMENTS

| | | |
|---|---|---|
| RU | 2143246 | 12/1999 |
| WO | 98/38920 | 9/1998 |
| WO | 01/21100 | 3/2001 |
| WO | 2006/021407 | 3/2006 |

* cited by examiner

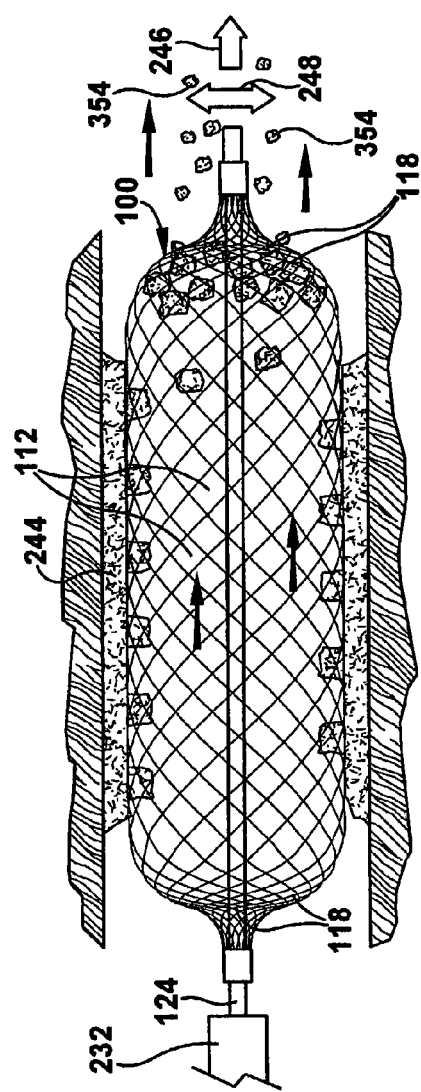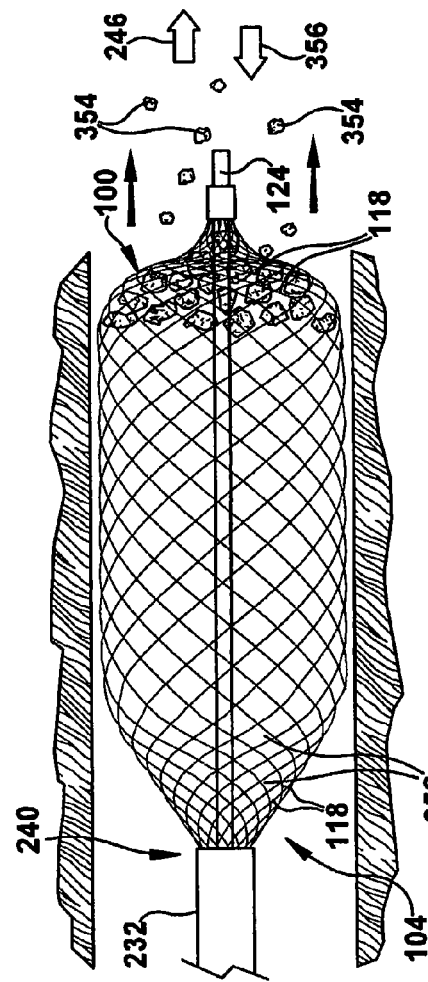

METHOD AND APPARATUS FOR INCREASING BLOOD FLOW THROUGH AN OBSTRUCTED BLOOD VESSEL

CROSS-REFERENCES TO RELATED APPLICATIONS

This application is a divisional of application Ser. No. 13/184,359, filed Jul. 15, 2011, now U.S. Pat. No. 8,317,748, which is a divisional application Ser. No. 11/700,987, filed Feb. 1, 2007, now U.S. Pat. No. 8,052,640, which is incorporated by reference in its entirety herein, and which claims priority from U.S. Provisional Application No. 60/764,206, filed Feb. 1, 2006 and U.S. Provisional Application No. 60/793,588, filed Apr. 20, 2006, the subject matter of both of which is incorporated herein by reference.

TECHNICAL FIELD

The present invention relates to an apparatus and method for increasing blood flow through an obstructed blood vessel and, more particularly, to a method and apparatus for using an expandable member to increase blood flow through an obstructed blood vessel.

BACKGROUND OF THE INVENTION

Vascular disease involves damage that happens to the blood vessels in the body. Diseased blood vessels can become plugged with thrombus, plaque, clots, grumous material, and/or other unwanted matter (hereafter "obstructions") that may ultimately lead to a condition known as ischemia. Ischemia refers to a substantial reduction or loss of blood flow to the brain or any other tissue that is being supplied by the blood vessel and can lead to permanent damage of the affected region. While vascular disease is most commonly associated with the formation of hard plaque and coronary artery disease in the heart, similar damage can happen to many other vessels in the body, such as the peripheral vessels and cerebral vessels, due to the buildup of obstructions, including hard plaque or softer thrombus/grumous material, within the lumen of an artery or vein.

A variety of vascular medical devices and procedures have been developed to treat diseased vessels. The current standard procedures include bypass surgery (where a new blood vessel is grafted around a narrowed or blocked artery) and several different types of non-surgical interventional vascular medical procedures, including angioplasty (a balloon on a catheter is inflated inside a narrowed or blocked portion of an artery in an attempt to push back the obstruction), lytic therapy (pharmaceutical agents are employed to chemically fragment the obstruction), stenting (a metal mesh tube is expanded against a narrowed or blocked portion of an artery to hold back the obstruction), and debulking techniques in the form of atherectomy (a high speed or high power mechanism is used to dislodge or mechanically abrade a hardened obstruction) or thrombectomy (a mechanism or infused fluid is used to dislodge/remove the obstruction). In each of these interventional vascular medical procedures, a thin, flexible guidewire is routed through the patient's vascular system to a desired treatment location and then a catheter, carrying a device appropriate for the given procedure, is tracked along the guidewire to the treatment location.

Although interventional vascular procedures avoid many of the complications involved in surgery, there is a possibility of complications if some of the obstruction breaks free and flows downstream in the blood vessel or into a connected blood vessel, potentially causing a stroke, a myocardial infarction (heart attack), or other tissue death. One solution to this potential complication is to use some kind of occlusive device or filtering device to block or screen the blood flowing downstream of the treatment location.

An example of a vascular filter is disclosed in U.S. Patent Application Publication No. 2002/0111648, published Aug. 15, 2002 by Richard S. Kusleika et al. (hereafter referenced as "the '648 publication"). The '648 publication discloses a collapsible medical device including a radially expandable body having proximal and distal sliders slidably attached to a mandrel (Abstract). The medical device is placed at a predetermined treatment site, such as a convenient location in a patient's vasculature positioned distally of an obstruction which will be treated with an angioplasty balloon or an atherectomy device (paragraph 0066). At least one embodiment of the medical device of the '648 publication can be used to filter fluid which is passing through a vessel and also can either temporarily or permanently occlude the vessel. The medical device of the '648 publication, however, may cause undue mechanical trauma or irritation to a previously healthy portion of the blood vessel because of the remote deployment from the obstruction site. Moreover, temporary or permanent occlusion of the blood vessel may cause ischemia and/or additional clotting of stagnant blood, thus adding to any such damage already caused by the unwanted obstruction.

SUMMARY OF THE INVENTION

In an embodiment of the present invention, a method of increasing blood flow through an obstructed blood vessel is described. An expandable member substantially made of a mesh having a plurality of interstices is provided. The expandable member has a proximal member end and a distal member end spaced longitudinally apart by a tubular member body. The expandable member is substantially closed at the distal member end. The expandable member is inserted into the blood vessel. The expandable member is positioned within the blood vessel with the proximal member end upstream of the distal member end and the member body located radially adjacent at least a portion of an obstruction. The expandable member is expanded to bring at least a portion of the member body into contact with the obstruction. An outward radial force is exerted on the obstruction to dislodge at least one fragment from the obstruction and to enhance blood flow through the blood vessel past the obstruction. The at least one fragment is passed through at least one interstice of the member body in the radial direction. The at least one fragment is selectively retained within the expandable member.

In an embodiment of the present invention, an expandable member is described. The expandable member includes a proximal member end and a distal member end, longitudinally spaced from the proximal member end. A tubular member body extends between the proximal and distal member ends and is adapted to selectively contact at least a portion of an obstruction within a blood vessel in a radial direction, to dislodge at least one fragment from the obstruction, and to enhance blood flow through the blood vessel past the obstruction. At least one of the proximal and distal member ends is closed. The member body is made of a first mesh having a plurality of first interstices. At least one of the first interstices is adapted to allow passage of at least one fragment therethrough in a radial direction into the member body. A closed one of the proximal and distal member ends is made of a second mesh having a plurality of second interstices. At least one of the second interstices is adapted to selectively allow passage of at least one fragment therethrough.

In an embodiment of the present invention, an apparatus for increasing blood flow through an obstructed blood vessel is described. A delivery catheter has proximal and distal catheter ends separated by a hollow catheter lumen and defining a longitudinal axis. The distal catheter end is adapted for placement within the blood vessel adjacent an obstruction. A guidewire has proximal and distal guidewire ends longitudinally separated by a guidewire body. The guidewire is adapted for selective insertion through the catheter lumen. An expandable member is removably attached to the guidewire adjacent the distal guidewire end; is selectively moveable between a first, collapsed condition and a second, expanded condition; and is adapted for passage through the catheter lumen in the collapsed condition and selective release from the catheter lumen and placement into the expanded condition adjacent the obstruction. The expandable member includes a proximal member end and a distal member end, longitudinally spaced from the proximal member end. A tubular member body extends between the proximal and distal member ends and is adapted to selectively contact at least a portion of the obstruction in a radial direction, to dislodge at least one fragment from the obstruction and to enhance blood flow through the blood vessel past the obstruction, when the expandable member is in the expanded condition. At least one of the proximal and distal member ends is closed. The tubular member body is made of a first mesh having a plurality of first interstices. At least one of the first interstices is adapted to allow passage of the at least one fragment therethrough in a radial direction into the member body. A closed one of the proximal and distal member ends is made of a second mesh having a plurality of second interstices. At least one of the second interstices is adapted to selectively allow passage of the at least one fragment therethrough.

BRIEF DESCRIPTION OF THE DRAWINGS

For a better understanding of the invention, reference may be made to the accompanying drawings, in which:

FIGS. 8A-8E are partial sectional views depicting a mechanism of operation of any embodiment of the present invention.

DETAILED DESCRIPTION OF THE PREFERRED EMBODIMENTS

Figure 1:
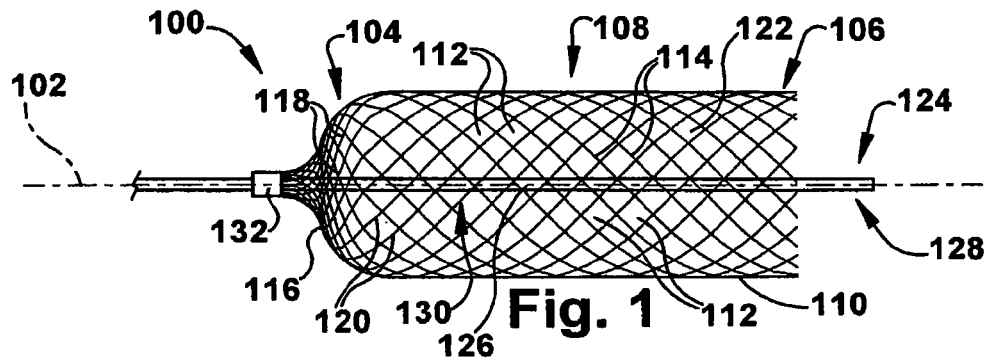
FIG. 1 is a side view of a first embodiment of the present invention.

In accordance with the present invention, FIG. 1 depicts a first arrangement of an expandable member 100 for increasing blood flow through an obstructed blood vessel. The expandable member 100 defines a longitudinal axis 102, which may be rectilinear or curvilinear. The expandable member 100 has a proximal member end 104 longitudinally spaced from a distal member end 106. The terms "proximal" and "distal" refer to orientations inside a patient's body with respect to a user, with a proximal location being nearer to an insertion point into the body than a distal location. It should be realized, however, that structures and deployment may be oriented differently for a particular application and that the terms "proximal" and "distal" are used herein for ease of description without limiting the present invention. At least one of the proximal and distal member ends 104 and 106 is closed, with a closed end, depicted as the proximal member end in FIG. 1, being positioned further downstream in a blood vessel than the rest of the expandable member 100. The expandable member 100 is selectively moveable between a first, collapsed condition and a second, expanded condition.

A tubular member body 108 extends between the proximal and distal member ends 104 and 106. The member body 108 is adapted to selectively contact at least a portion of an obstruction within a blood vessel in a radial direction, the radial direction being defined with respect to the longitudinal axis 102, and may exert a compressive force upon the obstruction. The member body 108 is also adapted to dislodge at least one fragment from the obstruction and to enhance blood flow through the blood vessel past the obstruction, with these functions being described in further detail below.

The member body 108 is made of a first mesh 110 having a plurality of first interstices 112. Each of the first interstices 112 is defined by a plurality of first strands 114. At least one of the first interstices 112 is adapted to allow passage of at least one fragment therethrough in a radial direction into the member body 108. A closed one of the proximal and distal member ends 104 and 106 (as shown in FIG. 1, the proximal member end) is made of a second mesh 116 having a plurality of second interstices 118. Each of the second interstices 118 is defined by a plurality of second strands 120. At least one of the second interstices 118 is adapted to selectively allow passage of at least one fragment therethrough. Many of the first and second interstices 112 and 118 and first and second strands 114 and 120 are left unlabeled in the Figures for clarity of depiction. Though the first interstices 112 are depicted in certain of the Figures as being larger than the second interstices 118 when there is an optional size difference between the two, the second interstices could instead be larger than the first interstices. Similarly, the sizes of the first interstices 112 could vary from one another and the sizes of the second interstices 118 need not be uniform either. It is contemplated that there could even be an overlap in size ranges between the first and second interstices 112 and 118.

Each of the first and second strands 114 and 120 may be oriented in at least one of a helical, longitudinal, and radial direction with respect to the member body 108. The first and second strands 114 and 120 may each be formed of any desired material or combination of materials, including, but not limited to, a metal, an alloy, a composite, a polymer, and the like. For example, the first and second strands 114 and 120 may each be made of nitinol, stainless steel, cobalt chromium, platinum, titanium, plastic, or any combination thereof. The first and second strands 114 and 120 may each have a diameter between about 10-250 microns, e.g., about 50 microns. Any of the first and second strands 114 and 120 may have a cross-sectional shape along at least a portion thereof which is designed to augment the performance of the expandable member 100 as described below. For example, the cross-sectional shape may include an angle designed to concentrate outward force of the expandable member at a specific portion of the strand cross-section periphery. Likewise, at least a portion of any of the first and second strands 114 and 120 could be coated with a material designed to produce a desired mechanical effect (e.g., cushioning, erosion, or any other effect) upon a surface contacted by the coated portion of the strand.

The first and second meshes 110 and 116 may be formed integrally or may be separately formed and attached together during manufacture of the expandable member 100. The first and second meshes 110 and 114 may each be at least partially constructed of a shape-memory material, such as nitinol. The first and second meshes 110 and 114 may be formed in any desired manner, including, but not limited to, braiding, welding, molding, weaving, laser-cutting a tube or sheet, and the like. The first and second meshes 110 and 114 should be configured for desired deployment characteristics, as described below, and to provide sufficient flexibility for tracking through a possibly tortuous vascular system of an individual, such as the intracranial vascular system.

Though the closed distal member end 106 is depicted in the Figures as having a tapered shape, the closed one (or both) of the proximal and distal member ends 104 and 106 can be of any suitable shape, such as, but not limited to, tubular, conical, convex, concave, or any other shape. Both of the proximal and distal member ends 104 and 106, when closed, may be made from the first mesh 110, the second mesh 116, or any other mesh (not shown) and need not be made from the same mesh. The below description will presume that each closed end is made from the second mesh 116. The shape of the closed one of the proximal and distal member ends 104 and 106 may be coincidentally produced by the method used to form the closed end(s) or may be formed intentionally for a desired performance effect.

The member body 108 defines a body interior 122. The expandable member 100 may include a guidewire 124 extending longitudinally between the proximal and distal member ends 104 and 106 through the body interior 122. The guidewire 124 may have an operative length 126 between the proximal and distal member ends 104 and 106 of between about 0.5-50 mm, e.g., about 22 mm. When present, the guidewire 124 has a proximal guidewire end (not shown) longitudinally separated from a distal guidewire end 128 by a guidewire body 130. The operative length 126 of the guidewire 124, between the proximal and distal member ends 104 and 106, is located adjacent the distal guidewire end 128.

The guidewire 124 may help push or pull the expandable member 100 through the vascular system to a desired deployment location. To this end, any suitable portion of the expandable member 100 may be attached to the guidewire 124 in a permanent manner (e.g., welding, crimping, soldering, adhesives, or the like) or by a temporary, releasable connection. If the latter, the connection mechanism (not shown) should be designed to be selectively releasable by the user as discussed below. The guidewire body 130 has a length sufficient to extend through the vascular system to place the expandable member 100 in the desired deployment location. For example, when the guidewire 124 is longitudinally connected to another structure (not shown) for moving the expandable member 100, the guidewire body 130 will be shorter than if the guidewire is the only structure that moves the expandable member. The guidewire body 130 may have a length of between about 0.5 mm-200 cm, e.g., about 150 cm. The diameter of the guidewire body 130 may vary along the length of the guidewire body or may be constant. For example, the diameter of the guidewire body 130 toward the proximal guidewire end may be between about 0.2-1 mm, e.g., about 0.36 mm, while the diameter of the operative length 126 portion of the guidewire body may be between about 0.05-1 mm, e.g., about 0.15 mm.

For clarity of description, the proximal member end 104 will be described below as being attached to the guidewire at or adjacent the distal guidewire end 128, unless otherwise specifically indicated. Regardless of the attachment type or means, the guidewire 124 may extend beyond at least one of the proximal and distal member ends 104 and 106 to support the expandable member 100, and may be adapted to removably or permanently attach the expandable member to a delivery system (not shown). The guidewire 124, when affixed, can facilitate minor changes in the position of the expandable member 100 during use and also can increase positional stability of the expandable member.

The expandable member 100 may include at least one radiopaque portion, such as the attachment collar 132 shown in FIG. 1, to facilitate remote visualization using, for example, one or more of fluoroscopy, computer tomography (CT) fluoroscopy, magnetic resonance, or the like. The radiopaque portion could be a structure of the expandable member 100 made of a radiopaque material or could be a separate radiopaque marker/material attached to or coated on at least a portion of the expandable member. For example, a thin layer of platinum could be sprayed, electroplated, or otherwise coated onto at least a portion of the expandable member 100.

Optionally, the expandable member 100 may be at least partially adapted to elute a pharmaceutical agent (not shown). As used herein, "eluting" means releasing, leaching, diffusing, or otherwise providing a pharmaceutical agent to a target area. The pharmaceutical agent may be impregnated in or coated on at least a portion of the expandable member 100, provided through a fluid connection between the expandable member and a pharmaceutical source (not shown), or otherwise directed to the target area via the expandable member 100. Alternately or additionally, a pharmaceutical agent may be provided to the patient locally or systemically in any desired dosage, using a mechanism other than the expandable member 100. Examples of suitable pharmaceutical agents for provision in any suitable manner include thrombolytic medication, anti-platelet medication, anti-thrombotic medication, a plasminogen activator (e.g., tPA, urokinase, streptokinase, desmotoplase), a IIb/IIIa inhibitor (e.g., abiciximab, tirofiban, eptifatide), a thrombin inhibitor (e.g., heparin, bivalirudin), or any combinations thereof.

Figure 2:
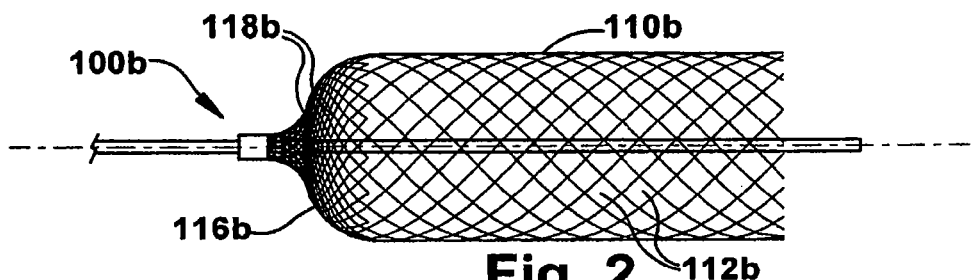
FIG. 2 is a side view of a second embodiment of the present invention.

FIG. 2 depicts a second embodiment of an expandable member 100b according to the present invention. The expandable member 100b of FIG. 2 is similar to the expandable member 100 of FIG. 1 and therefore, structures of FIG. 2 that are the same as or similar to those described with reference to FIG. 1 have the same reference numbers with the addition of a "b". Description of common elements and operation similar to those in the previously described embodiment will not be repeated with respect to the second embodiment.

As with the first embodiment, the first and second meshes 110b and 116b of the second embodiment may be formed integrally or may be separately provided and attached before use. As shown in FIG. 2, however, at least one of the plurality of second interstices 118b may be smaller than at least one of the plurality of first interstices 112b.

Figure 3:
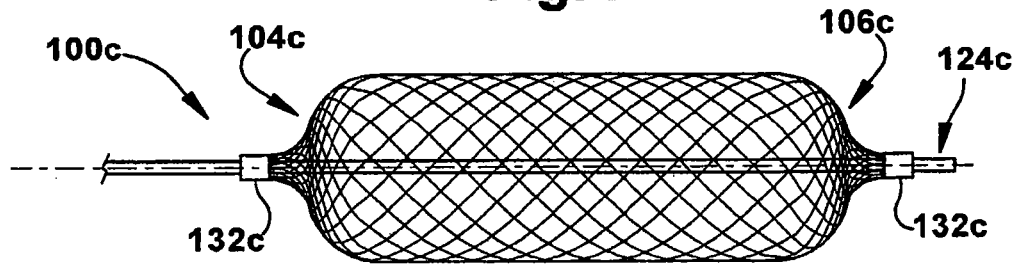
FIG. 3 is a side view of a third embodiment of the present invention.

FIG. 3 depicts a third embodiment of an expandable member 100c according to the present invention. The expandable member 100c of FIG. 3 is similar to the expandable member 100 of FIG. 1 and therefore, structures of FIG. 3 that are the same as or similar to those described with reference to FIG. 1 have the same reference numbers with the addition of a "c". Description of common elements and operation similar to those in the previously described embodiments will not be repeated with respect to the third embodiment.

In the third embodiment, and as shown in FIG. 3, both the proximal and distal ends 104c and 106c are closed. Additionally, the proximal and distal ends 104c and 106c are both shown as being connected to the guidewire 124c through attachment collars 132c. Either or both of the attachment collars 132c depicted in FIG. 3, or any other portions of the expandable member 100c, may be radiopaque.

Figure 4:
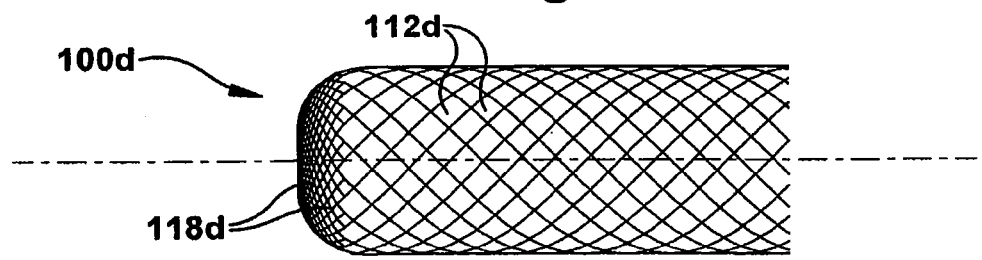
FIG. 4 is a side view of a fourth embodiment of the present invention.

FIG. 4 depicts a fourth embodiment of an expandable member 100d according to the present invention. The expandable member 100d of FIG. 4 is similar to the expandable member 100 of FIG. 1 and therefore, structures of FIG. 4 that are the same as or similar to those described with reference to FIG. 1 have the same reference numbers with the addition of a "d". Description of common elements and operation similar to those in the previously described embodiments will not be repeated with respect to the fourth embodiment.

Similarly to the second embodiment, the fourth embodiment includes first interstices 112d which are a different size than the second interstices 118d. The expandable member 100d shown in FIG. 4 omits the previously described guidewire. However, one of ordinary skill in the art can readily design a suitable deployment mechanism for an expandable member 100d lacking a guidewire, and the description of operation of the present invention (below) will presume that a guidewire is present, notwithstanding the depiction of FIG. 4.

Figure 5:
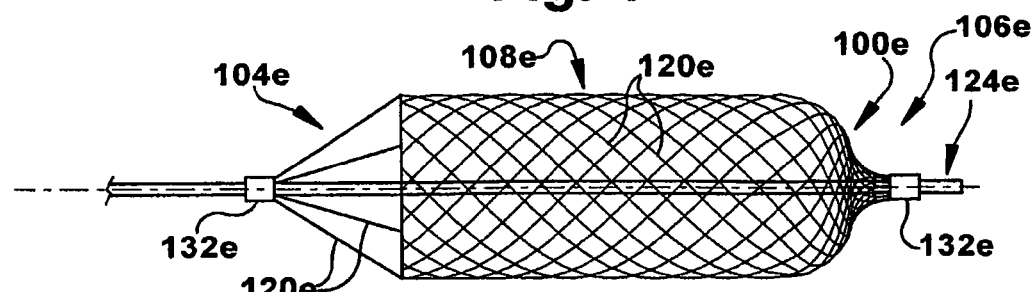
FIG. 5 is a side view of a fifth embodiment of the present invention.

FIG. 5 depicts a fifth embodiment of an expandable member 100e according to the present invention. The expandable member 100e of FIG. 5 is similar to the expandable member 100 of FIG. 1 and therefore, structures of FIG. 5 that are the same as or similar to those described with reference to FIG. 1 have the same reference numbers with the addition of a "e". Description of common elements and operation similar to those in the previously described embodiment will not be repeated with respect to the fifth embodiment.

FIG. 5 illustrates an expandable member 100e similar to that of the third embodiment, in which both the proximal and distal ends 104e and 106e are closed. Additionally, the proximal and distal ends 104e and 106e are both shown as being connected to the guidewire 124e through attachment collars 132e. The proximal end 104e is not made of a tightly woven mesh, however, but instead includes a small number of second strands 120e (four shown) linking the member body 108e to the attachment collar 132e.

Regardless of the embodiment of the expandable member 100, the present invention may be used to help increase blood flow through an obstructed blood vessel by both compressing and fragmenting the obstructing matter. FIGS. 6A-6C and 7A-7D depict first and second modes of operation, respectively, of the deployment of an expandable member 100 according to the present invention. Although the expandable member 100 is described in a vascular application, the present invention may readily be used in other body lumens, as will be appreciated by one of ordinary skill in the art.

Figure 6A:
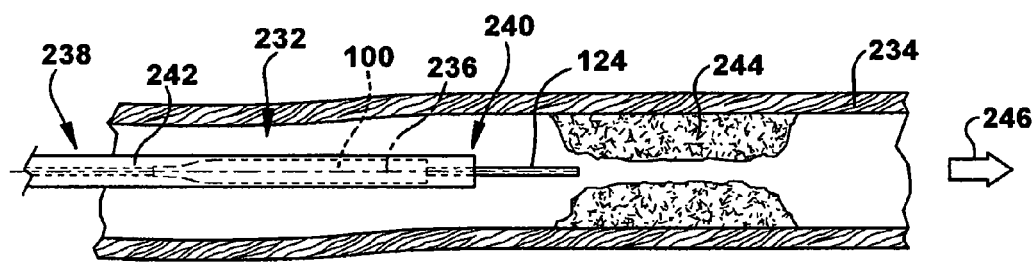
FIGS. 6A-6C are partial sectional views depicting the embodiment of FIG. 1 in a first mode of operation.

A delivery catheter 232 may be inserted into a blood vessel 234 in any suitable manner, such as through the use of endovascular, percutaneous, or other minimally invasive surgical techniques. The delivery catheter 232 defines a longitudinal axis 236, which may be rectilinear or curvilinear. The delivery catheter 232 has proximal and distal catheter ends 238 and 240, respectively, separated by a hollow catheter lumen 242. The distal catheter end 240 is adapted for placement within the blood vessel 234 adjacent an obstruction 244, as shown in FIG. 6A. A nonlimiting example of a suitable delivery catheter is one of the Excelsior line of microcatheters, available from Boston Scientific of Natick, Mass. The 1.5-3 French sized Excelsior microcatheters, for example, may be useful in an intracranial application of the present invention.

The obstruction 244 may include any material that fully or partially blocks a blood vessel 234, such as a thrombus. The thrombus can arise due to conditions such as a cardioembolism, a carotid bifurcation, or an iatrogenic cause of idiopathic or cryptogenic etiology. Plaque, clots, grumous material, and/or other unwanted matter could also or instead form the obstruction 244. Several of the Figures are partial side or sectional views depicting the obstruction 244 in cross-section as a cylindrical obstruction lining the blood vessel 234, but discontinuous patches of obstruction could also or instead be present. The obstruction 244 may not be tightly adhered to the blood vessel 234, but may be loosely held in position within the blood vessel, or could even be floating freely in the body. In the latter two cases, the expandable member 100 can be used to trap the obstruction 244 against a wall of the blood vessel 234. The blood vessel 234 may be of the intracranial cerebrovasculature, such as an internal carotid artery, a middle cerebral artery, an anterior cerebral artery, a vertebral basilar artery, or a posterior cerebral artery, or may be in any other body lumen or vessel.

Figure 6B:
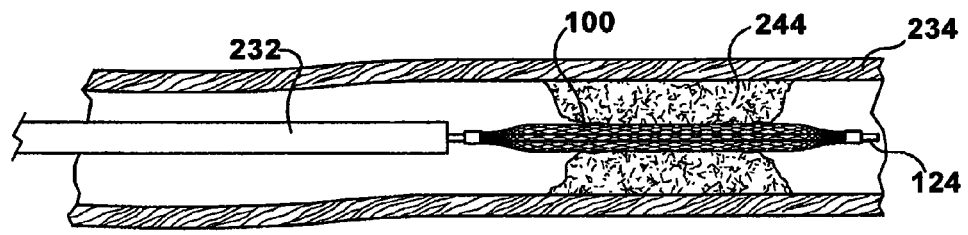
Figure 6C:
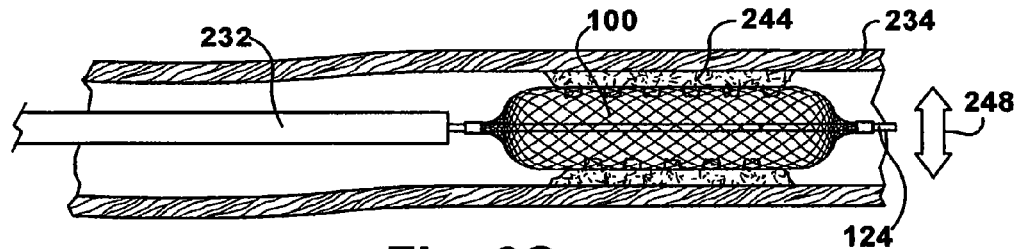

As previously mentioned, the terms "proximal" and "distal" are used herein for clarity of description and do not limit the positioning or arrangement of the structures of the present invention. In the orientation of FIGS. 6A-6C, blood within the vessel flows in a bloodstream 246 direction, from the proximal catheter end 238 toward the distal catheter end 240, and the obstruction 244 is accessed from upstream. Since the bloodstream 246 may assist the operation of the expandable member 100, one of ordinary skill in the art can readily design a suitable expandable member and corresponding deployment apparatus which may be used in the opposite instance, when the obstruction 244 is accessed from downstream (not shown).

In FIG. 6A, the expandable member 100, in dashed line, is in the first, collapsed condition within the catheter lumen 242. The expandable member 100 is attached to the guidewire 124, which is adapted for selective insertion through the catheter lumen 242. As the guidewire 124 travels through the catheter lumen 242, the expandable member 100 is carried to the obstruction 244. At least one of the delivery catheter 232, guidewire 124, and expandable member 100 may include at least one radiopaque portion/marker (not shown) to aid the user in visualizing the position of the marked structure throughout the deployment procedure.

In FIG. 6B, the expandable member 100 is still in the collapsed condition, but has exited the distal catheter end 240 and is located adjacent the obstruction 244. The site of deployment of all or a portion of the expandable member 100 is typically radially within the obstruction 244. However, the site of deployment can also be upstream or downstream of the obstruction 244, with the expandable member 100 being moved, in a collapsed or partially expanded condition, to a position radially within the obstruction. The obstruction 244 need not entirely radially surround the expandable member 100; instead, the expandable member could be deployed radially off-center with respect to the obstruction, or the obstruction 244 may not entirely cover the inner circumference of the blood vessel 234.

Generally in an intracranial application, the diameter of the expandable member 100 may be between about 0.05-5 mm, e.g., about 0.016 mm, in the collapsed state and between about 0.1-10 mm, e.g., about 5 mm, in the expanded state. Similarly, and again for an intracranial application, the length of the expandable member 100 may be between about 5-60 mm, e.g., about 22 mm, in both the collapsed and expanded states, unless the design structure of the expandable member causes appreciable length change during radial expansion and collapse. The dimensions of the expandable member 100, like all structures described herein, are highly dependent upon the dimensions of the delivery catheter and body lumen in which the expandable member 100 travels and is deployed, respectively, and one of ordinary skill in the art can readily choose appropriate dimensions for all structures used in a particular application of the present invention.

Turning to FIG. 6C, the expandable member 100 is shown in the second, expanded condition within at least a portion of the obstruction 244. The arrow depicting the expansion direction 248 indicates that a radially outward force is exerted by the expandable member 100 against the adjacent obstruction 244. Though the expansion direction 248 is shown as being two-dimensional, the expandable member 100 will expand radially in all directions outward from the longitudinal axis 102 unless the expandable member has been designed/configured for nonuniform expansion.

In the sequence of FIG. 6A-6C, the expandable member 100 exits the delivery catheter 232 in the collapsed condition and is placed in the desired position adjacent the obstruction 244 before being expanded into the expanded condition. The expandable member 100 shown in FIGS. 6A-6C may self-expand once in position, for example, through use of a temperature-respondent shape-memory alloy. Alternately or additionally, the expandable member 100 may be manually expanded through use of an inflation balloon (not shown), in a known manner. That is, an inflation catheter (not shown) carrying the inflation balloon may be provided for selective insertion through the catheter lumen 242. The expandable member 100 is optionally crimped around the inflation balloon when in the collapsed condition. In such a case, the inflation catheter may replace the guidewire 124 in performing the function of guiding and/or carrying the expandable member 100 to the site of the obstruction 244. The inflation catheter, through the inflation balloon, then may be operative to selectively manually expand the expandable member 100 adjacent at least a portion of the obstruction 244. When an inflation balloon is used to expand the expandable member 100, the inflation balloon may be configured so as not to block the first interstices 112 while the inflation balloon still exerts radially outward pressure on the expandable member, to help provide compression and fragmentation of the obstruction 244 as described below.

In the sequence of FIGS. 7A-7D, a second mode of operation of the expandable member 100 is depicted. As with the first mode of operation, a delivery catheter 232 is advanced downstream through a blood vessel 234 to a position adjacent an obstruction 244. However, in the second mode of operation, the expandable member 100 is at least partially constructed of a superelastic and/or self-expanding material, such as nitinol which has been memory-shaped into an expanded condition and is compressed into a collapsed condition before use. Therefore, the expandable member 100 is constrained in the collapsed condition by the delivery catheter 232 and self-expands into the expanded condition upon removal from the delivery catheter.

Figure 7A:
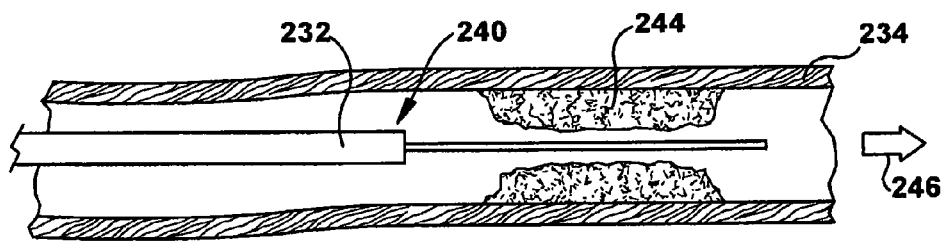
FIGS. 7A-7D are partial sectional views depicting the embodiment of FIG. 1 in a second mode of operation.
Figure 7B:
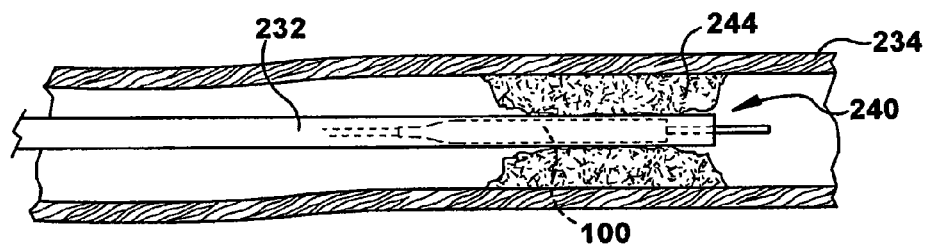

FIG. 7A depicts the delivery catheter 232 with the guidewire 124 extending from the distal catheter end 240 and through the obstruction 244. In FIG. 7B, the delivery catheter 232 has been advanced over the guidewire 124 until the distal catheter end 240 is located radially adjacent at least a portion of the obstruction 244. The expandable member 100, shown in dashed line in FIG. 7B within the delivery catheter 232, is also located radially adjacent at least a portion of the obstruction 244. Though the guidewire 124 is shown and described as guiding both the expandable member 100 and the delivery catheter 232, a secondary guidewire (not shown) may be provided to assist in positioning the delivery catheter; the secondary guidewire could then be exchanged for the guidewire 124 for deployment of the expandable member.

Figure 7C:
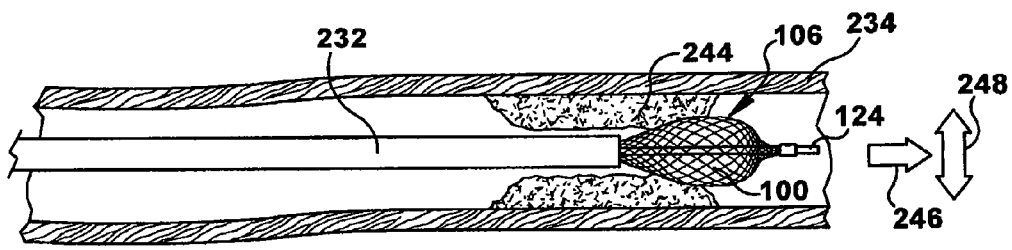

During the transition from the view of FIG. 7B to that of FIG. 7C, the expandable member 100 is maintained in position within the obstruction 244 while the delivery catheter 232 is withdrawn in a proximal direction from the expandable member, thus exposing the distal member end 106. Because the expandable member 100 in the second mode of operation is self-expanding, the distal member end 106 begins to expand in a known manner in the expansion direction 248 as the expandable member is released by the delivery catheter 232.

Figure 7D:
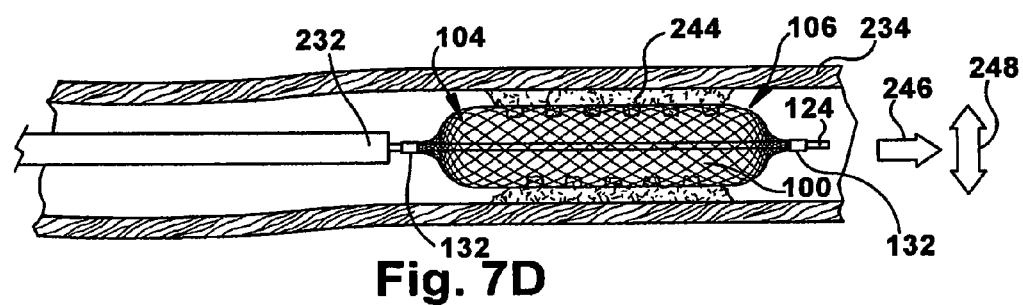

FIG. 7D depicts the self-expanding expandable member 100 of the second mode of operation in a fully expanded condition adjacent the obstruction 244. Since the blood flow direction 246 in the orientation of FIGS. 7A-7D moves proximal-to-distal, it is desirable for the distal member end 106 to be closed and to be located downstream of the proximal member end 104, which is also shown in FIGS. 7A-7D as being closed. As can be seen in FIG. 7D, the proximal and distal member ends 104 and 106 may be connected to the guidewire 124 by the attachment collars 132.

As can be seen in the sequences of FIGS. 6A-6C and 7A-7D, the obstruction 244 becomes at least partially compressed against the blood vessel 234 as the expandable member 100 expands, regardless of the means by which such expansion occurs. This compression aids in increasing blood flow past the obstruction 244. The sequence of FIGS. 8A-8E depicts both this compression and a separate erosion-type process as a combined mechanism of operation through which any embodiment of the present invention increases blood flow through the obstructed blood vessel 234.

Figure 8A:
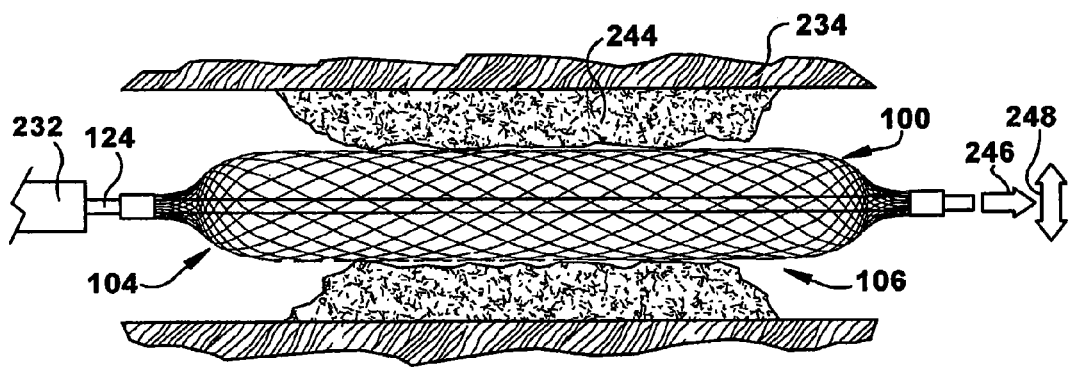

In FIG. 8A, the expandable member 100 is positioned adjacent the obstruction 244 with the proximal member end 104 located upstream of the distal member end 106 (both shown here as being closed). The blood flow direction 246 is from left to right, in the orientation of FIGS. 8A-8E, and the expandable member 100 is exerting outward radial force in the expansion direction 248. The force exerted by the expandable member 100 depends on a number of factors, which include the properties of the material chosen for the expandable member. By suitably varying these factors, the force exerted by the expandable member 100 can be controlled. The expandable member 100 may exert sufficient force to cause the member body 108, or another portion of the expandable member, to compress at least a portion of the obstruction 244 against a vessel wall 350 of the blood vessel 234.

Figure 8B:
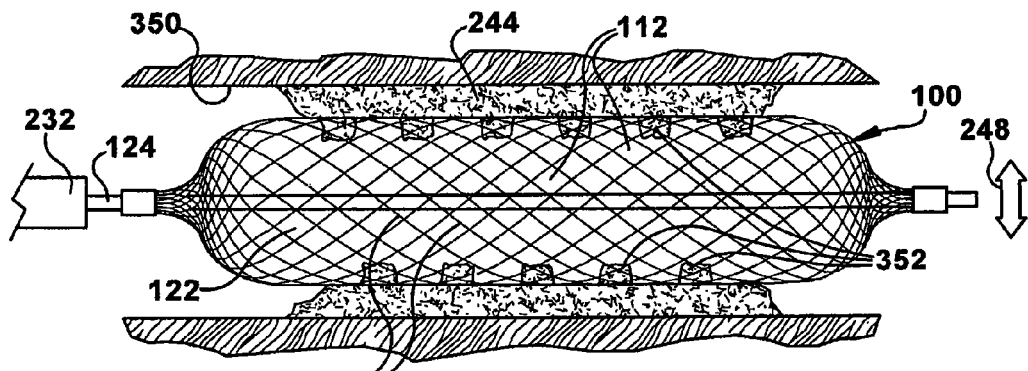

In FIG. 8B, the force exerted by the expandable member 100 dislodges at least one fragment 352 from the obstruction 244 and helps pass each fragment 352 through a first interstice 112 in the radial direction into the body interior 122. In other words, at least one of the plurality of first strands 114 may penetrate into the obstruction 244 to longitudinally separate each fragment 352 from a remaining portion of the obstruction.

The action by which the expandable member 100 dislodges the fragments 352 may vary depending upon the composition of the obstruction 244. For example, when the obstruction 244 is made up of a relatively soft material, the first strands 114 may slice radially into the obstruction 244 and the fragments 352 will protrude into the expandable member 100 in an extruding manner. If the obstruction 244 is made up of a harder material, pressure from the first strands 114 may instead flake off fragments 352 in a fracturing manner.

Optionally, the expandable member 100 may be adapted for at least a small degree of rotation about the longitudinal axis 102. Such rotation, once the first strands 114 are at least partially embedded in the obstruction 244, may help to free the fragments 352 from the obstruction 244 by severance in a circumferential direction about the longitudinal axis 102.

Figure 8C:
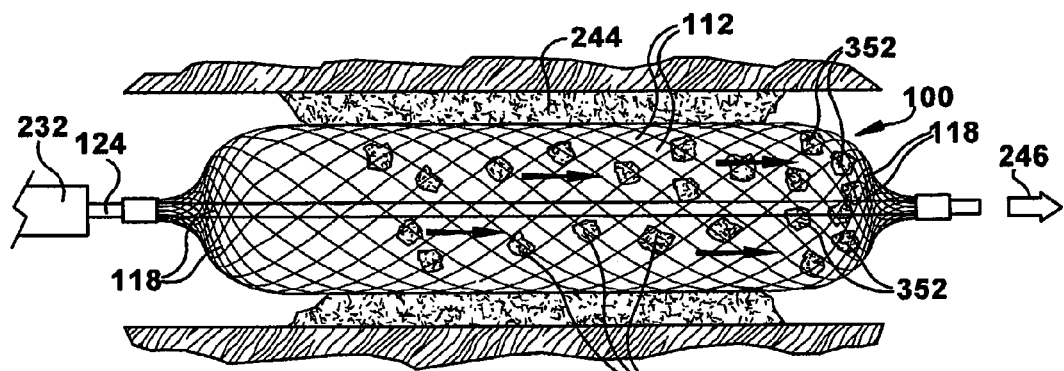

Whether or not the expandable member 100 is rotated, blood flowing in the blood flow direction 246 will exert pressure on the fragments 352 to help separate the fragments from the obstruction 244. The fragments 352, once free within the member body 108, are then carried by the blood in the blood flow direction 246 toward the (closed) distal member end 106, where the fragments collect as shown in FIG. 8C.

If one or more of the fragments 352 is smaller than one of the second interstices 118, the fragment will pass through that second interstice and out of the expandable member 100 in a downstream direction. To this end, the size of at least one of the plurality of first interstices 112 and/or the plurality of second interstices 118 may be chosen depending upon an allowable particulate size of the blood vessel 234. This allowable particulate size may vary, depending upon the size and location of the blood vessel 234, the size and location of other vasculature in fluid connection downstream from the blood vessel 234, the presence of any pharmaceutical agents and/or other medical devices within the blood vessel 234, or any other factors. The size of fragment 352 which may pass through the first and second interstices 112 and 118 will vary depending upon at least the position of that interstice on the member body 108, the degree of expansion of the expandable member 100, the shape of the fragment 352, and the orientation of the interstice with respect to the blood flow direction 246. For example, if a certain interstice (particularly a second interstice 118) is oriented substantially perpendicularly to the longitudinal axis 108, a larger fragment 352 may more readily pass through that interstice than if the interstice were at an oblique angle with respect to the longitudinal axis. One of ordinary skill in the art can readily design first and second meshes 110 and 116 having desired properties to selectively retain the fragments 352 in a suitable manner for a particular application of the present invention.

If a fragment 352 is too large to pass through a second interstice 118 and flow downstream of the expandable member 100, at least one of the plurality of second strands 120 may break the fragment into a plurality of subfragments 354. At least one of the second interstices 118 may then allow passage therethrough of at least one subfragment 354 to release the subfragment 354 from the expandable member 100. The second strand 120 breaks the fragment 352 into subfragments 354 in a similar manner to that in which the first strand 114 dislodges the fragment from the obstruction 244. Namely, pressure exerted on the fragment 352 in the blood flow direction 246 by flowing blood and/or other fragments collected at the distal member end 106 forces the fragment into contact with the second strand 120. When the pressure becomes sufficient to overcome the mechanical resistance of the fragment 352, the fragment begins to be extruded or fractured through the second interstice 118, as shown in FIG. 8D. The subfragments 354 thereby formed exit the expandable member 100 and are carried away from the site of the obstruction 244 by blood flow through the blood vessel 234.

In addition to this mechanical lysing provided by the second strands 120, the fragments 352 could also undergo chemical lysing to enhance the breakup of the obstruction 244. A pharmaceutical agent (not shown) could be provided to at least partially lyse at least one fragment 352 and/or subfragment 354. The pharmaceutical agent may be eluted by the expandable member 100, as previously mentioned. Additionally or alternatively, the pharmaceutical agent may be provided via the delivery catheter 232 at a location adjacent the obstruction 244. Moreover, the pharmaceutical agent could be locally or systemically provided to the patient in another manner. Regardless of the manner of provision of the pharmaceutical agent, chemical lysing will be operative upon at least one of the obstruction 244, a fragment 352, and/or a subfragment 354. Chemical lysing agents are most effective upon structures having a large ratio of surface area to volume, so it is advantageous to mechanically break up the obstruction 244 into smaller pieces (such as fragments 352 and/or subfragments 354) to decrease the time required for the obstruction 244 to chemically lyse.

As shown in FIG. 8D, the expandable member 100 continues to exert pressure upon the obstruction 244 in the expansion direction 248 as fragments 352 are dislodged from the obstruction. Therefore, as the volume of the obstruction 244 is reduced by loss of the fragments 352 and/or by compression of the obstruction 244 toward the vessel wall 350, more blood will be able to flow through the volume-diminished obstruction 244. The increased blood flow past the obstruction 244 will help to mechanically lyse the obstruction, whether or not the expandable member 100 continues to dislodge fragments 352 from the obstruction. Stasis (e.g., that caused by an obstruction 244) in a blood vessel 234 allows for factors which promote obstructions to accumulate, thereby maintaining the obstruction in the blood vessel. Reestablishing or enhancing blood flow washes away and dilutes these factors and promotes erosion of the obstruction 244. Additionally, the increased blood flow will exert increased pressure on the collected fragments 352 at the distal member end 106, potentially enhancing the mechanical lysing of the fragments into subfragments 354.

Optionally, an aspiration catheter (not shown) is adapted for selective insertion through the catheter lumen 242. The aspiration catheter, when present, is operative to selectively remove at least one fragment 352 from the expandable member 100 under suction power. The aspiration catheter may place the body interior 122 into direct fluid communication with a suction source (not shown) to directly remove the fragment 352 from within the expandable member 100. Alternately, the aspiration catheter may exert suction power upon the fragment 352 from an outside position adjacent the proximal or distal member ends 104 or 106 to supplement the pressure naturally provided in the blood flow direction 246 and thereby pull the fragment through a second interstice 118, either into the aspiration catheter for removal from the body or to enhance release of the fragment into the blood vessel 234 downstream of the expansion member 100. The use of such an aspiration catheter may be desirable if fragments 352 collecting at the distal member end 106 are not exiting the expandable member 100 and are reducing blood flow through the expandable member in an unwanted manner.

Once the obstruction 244 has been fragmented and depleted as desired, the expandable member 100 may be collapsed from the expanded condition to the collapsed condition and removed from the blood vessel 234 through the delivery catheter 232. FIG. 8E depicts the expandable member 100 in the process of collapsing. The expandable member 100 is maintained in position inside the blood vessel 234, and the delivery catheter is moved in a sheathing direction 356 (opposite the blood flow direction 246) to envelop the expandable member. The expandable member 100 will be constrained into the collapsed condition upon contact with the distal catheter end 240 and can then be held within the catheter lumen 242 for removal from the blood vessel 234.

In another, alternate mode of removal (not shown), the delivery catheter 232 could be maintained in position so that the guidewire 124 can be pulled in the blood flow direction 246. The guidewire in this alternate removal mode thus pulls an attached expandable member 100 into a relatively stationary delivery catheter. However, care should be taken during movement of the expandable member 100 to avoid mechanical trauma to the vessel wall 350. In any mode of removal, the delivery catheter 232 and the expandable member 100 can both or either move to produce a relative sheathing motion between these two structures.

It is contemplated that the expandable member 100 can be collapsed from the expanded condition into the collapsed condition in any suitable manner, and then moved rotationally and/or longitudinally within the blood vessel 234 while constrained, such as through a motion of the delivery catheter 232 enclosing the expandable member. The expandable member 100, once positioned as desired, may then be re-expanded from the collapsed condition to the expanded condition. Such redeployment may be useful, for example, when the obstruction 244 has a longitudinal dimension greater than that of the expandable member 100 or when the same expandable member is operative on a plurality of spaced-apart obstructions 244. The expandable member 100 may be collapsed and redeployed any number of times, as desired by the user.

Regardless of whether the expandable member 100 is redeployed within the blood vessel 234, it may be desirable to finally remove the expandable member from the blood vessel once a suitable blood flow rate is reinstated in the blood vessel across the site of the treated obstruction 244. For example, angiography can be performed to assess blood flow, with additional mechanical and/or chemical lysing being performed until the blood flow has achieved a suitable rate for a predetermined period of time—for example, between about 10-15 minutes.

When the expandable member 100 is removed from the patient's body, acute and chronic anti-platelet therapy is no longer necessary to prevent the expandable member from causing future obstructions. Such acute and chronic anti-platelet therapy may increase the likelihood of development of complication, such as an intracranial hemorrhage, associated with other methods of acute revascularization. An intracranial hemorrhage occurring when the patient's system contains pharmaceutical agents for chemical lysing may be fatal. Even when no chemical lysing or anti-platelet agents are present, surgical treatment for an intracranial hemorrhage is fraught with postoperative complications. Therefore, it may be desirable for the expandable member 100 to be removed from the patient's body.

Optionally, the expandable member 100 may be removed from the blood vessel 234 before the structures of the expandable member heal into the vessel wall 350. For example, the expandable member 100 may be removed in the above manner from about one (1) minute to about 48 hours after delivery of the device, with re-operation possibly being required for removal toward the latter portion of that range of time. However, when the expandable member 100 is intended to remain in the patient's body for an extended period of time, the expandable member should be adapted for release from the guidewire 124, preferably when the expandable member is in the expanded condition at the desired implantation location within the blood vessel 234. The release may be carried out in any suitable manner, using any desired mechanical, chemical, electrolytic, temperature-sensitive, remotely-triggered, or other type of release means.

At least one fragment 352 may be carried from the blood vessel 234 within the expandable member 100 as the expandable member is withdrawn through the delivery catheter 232. Additionally, the force exerted by the distal catheter end 240 on the expandable member 100 may squeeze the fragments 352 collected at the distal member end 106 against the first or second strands 114 or 120. Such squeezing force may cause extrusion or flaking of the fragments into subfragments 354, which are then released into the blood vessel 234 as shown in FIG. 8E. The first and second meshes 110 and 116 should be designed such that these delayed subfragments 354 do not exceed the allowable particulate size of the blood vessel 234.

While aspects of the present invention have been particularly shown and described with reference to the preferred embodiment above, it will be understood by those of ordinary skill in the art that various additional embodiments may be contemplated without departing from the spirit and scope of the present invention. For example, the member body 108 could have a round, ovoid, rectilinear, curvilinear, or any other desired cross-sectional shape. The expandable member 100 can expand or collapse in a radial, circumferential, and/or longitudinal direction. Like all described structures, the expandable member 100 may be made of any materials and in any dimensions, as appropriate for a particular application of the present invention. The expanded and collapsed conditions of the expandable member 100 are not strict binary limits upon the condition of the expandable member, but represent more general ranges of condition (e.g., an expandable member in the "expanded" condition may be able to expand further as the obstruction 244 is eroded and/or compressed). Several of the first strands 114 may perform functions of the second strands 120 and vice versa, particularly if the divisions between the member body 108 and proximal/distal member ends 104 and 106 are not sharply delineated. Likewise, certain strands may function as both first and second strands 114 and 120 at various points along the length thereof. The expandable member 100 can be used in conjunction with lytic agents (tPA and IIb/IIIa inhibitors), and can also be used with various microcatheters, guidewires and endovascular access devices that are currently commercially available. Operation of the expandable member 100 is described as being assisted by bloodflow within the blood vessel 234, but the present invention is also operable when blood flow is intentionally or inadvertently reduced or eliminated within the blood vessel 234. The expandable member 100 is described as performing a filtering function upon fragments 352 dislodged from the obstruction 244, but could also or instead provide a filtering function to existing fragments (not shown) in the bloodstream which did not originate with the obstruction. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

We claim:

1. An expandable member and a delivery system for removing an obstruction from a blood vessel, comprising:
   a delivery system; and
   an expandable member comprising:
   a proximal member end permanently attached to the delivery system;
   a distal member end;
   a member body extending between the proximal and distal member ends and, the member body expandable from a first diameter to a second diameter, the second diameter being larger than the first diameter, such that when the member body is expanded to the second diameter, the member body contacts at least a portion of the obstruction within a blood vessel to enhance blood flow through the blood vessel; and said member body further comprising at least a portion of the member body made of a first mesh having a plurality of first interstices, at least one of the first interstices being adapted to allow passage of at least one dislodged portion of the obstruction therethrough in a radial direction into the member body.

2. The expandable member and the delivery system of claim 1, wherein the obstruction is dislodged by fracturing a portion of the obstruction.

3. The expandable member and the delivery system of claim 1, wherein the obstruction is dislodged by extruding a portion of the obstruction.

4. The expandable member and the delivery system of claim 1, wherein the expandable member includes at least one radiopaque portion.

5. The expandable member and the delivery system of claim 1, said expandable member being at least partially constructed of a self-expanding material.

6. The expandable member and the delivery system of claim 1, wherein the blood vessel is a cerebral blood vessel.

7. The expandable member and the delivery system of claim 1, said expandable member being at least partially adapted to elute a pharmaceutical agent.

8. The expandable member and the delivery system of claim 7, wherein the pharmaceutical agent is adapted to at least partially lyse at least one fragment of the at least one dislodged portion of the obstruction.

9. The expandable member and the delivery system of claim 1, wherein the proximal member end of the expandable member is closed and is made of a second mesh having a plurality of second interstices, at least one of the second interstices being adapted to selectively allow passage of at least one fragment therethrough.

10. The expandable member and the delivery system of claim 9, wherein said first mesh is formed integrally with the second mesh.

11. The expandable member and the delivery system of claim 9, wherein at least one of the plurality of second interstices is smaller than at least one of the plurality of first interstices.

12. The expandable member and the delivery system of claim 9, wherein the size of at least one of the plurality of second interstices is chosen depending upon an allowable particulate size of the blood vessel.

13. The expandable member and the delivery system of claim 1, wherein at least one of the first interstices is defined by a plurality of first strands, and at least one of the plurality of first strands is adapted to penetrate into the obstruction to longitudinally separate at least one fragment of the at least one dislodged portion of the obstruction from a remaining portion of the obstruction.

14. The expandable member and the delivery system of claim 1, wherein the proximal member end of the expandable member is closed and is made of a second mesh having a plurality of second interstices, said first mesh is formed integrally with the second mesh, and at least one of the second interstices is defined by a plurality of second strands, at least one of the plurality of second strands is adapted to break at least one fragment of the at least one dislodged portion of the obstruction into a plurality of subfragments, and at least one of the second interstices is adapted to selectively allow passage therethrough of at least one subfragment to release the at least one subfragment from the expandable member.

15. The expandable member and the delivery system of claim 1, wherein the member body is adapted to compress at least a portion of the obstruction against a vessel wall of the blood vessel.

16. The expandable member and the delivery system of claim 1, wherein the member body defines a body interior, the expandable member including a guidewire extending longitudinally between the distal and proximal member ends through the body interior, the guidewire being attached to a closed one of the distal and proximal member ends.

17. The expandable member and the delivery system of claim 16, wherein the guidewire extends beyond at least one of the distal and proximal member ends and is adapted to permanently attach the expandable member to the delivery system.

18. The expandable member and the delivery system of claim 1, wherein the expandable member includes a plurality of strands forming the first mesh and a second mesh and wherein each of the strands is oriented in at least one of a helical, longitudinal, and radial direction with respect to the member body.

19. The expandable member and the delivery system of claim 1, wherein said distal member end of the expandable member is open.

20. The expandable member and the delivery system of claim 1, wherein the member body of the expandable member is tubular in shape.

* * * * *